(12) United States Patent
Picard et al.

(10) Patent No.: US 7,115,772 B2
(45) Date of Patent: Oct. 3, 2006

(54) INTEGRATED PROCESS FOR PRODUCING CARBONYLATION ACETIC ACID, ACETIC ANHYDRIDE, OR COPRODUCTION OF EACH FROM A METHYL ACETATE BY-PRODUCT STREAM

(75) Inventors: Wayne David Picard, Houston, TX (US); Mark O. Scates, Houston, TX (US); Stephen Charles Webb, Clear Lake Shores, TX (US); Duane Lyle Usrey, Paducah, KY (US)

(73) Assignee: Celanese International Corporation, Dallas, TX (US)

( * ) Notice: Subject to any disclaimer, the term of this patent is extended or adjusted under 35 U.S.C. 154(b) by 446 days.

(21) Appl. No.: 10/324,648

(22) Filed: Dec. 19, 2002

(65) Prior Publication Data

US 2003/0135070 A1   Jul. 17, 2003

Related U.S. Application Data

(60) Provisional application No. 60/347,532, filed on Jan. 11, 2002.

(51) Int. Cl.
  *C07C 67/48* (2006.01)
(52) U.S. Cl. ........................... 560/248; 560/231
(58) Field of Classification Search ............... None
  See application file for complete search history.

(56) References Cited

U.S. PATENT DOCUMENTS

| | | |
|---|---|---|
| 4,234,718 A | 11/1980 | Brown |
| 4,234,719 A | 11/1980 | Wan |
| 4,352,940 A | 10/1982 | Adelman |
| 4,544,511 A | 10/1985 | Isshiki et al. |
| 5,001,259 A | 3/1991 | Smith et al. |
| 5,144,068 A | 9/1992 | Smith et al. |
| 5,206,434 A | 4/1993 | Scates et al. |
| 5,770,770 A | 6/1998 | Kim et al. |
| 5,831,120 A | 11/1998 | Watson et al. |

FOREIGN PATENT DOCUMENTS

| | | |
|---|---|---|
| EP | 0 087 870 | 4/1985 |
| EP | 0 108 437 | 5/1986 |
| EP | 1 061 063 | 12/2000 |
| GB | 2 013 184 A | 8/1979 |
| JP | 60-60107 | 6/1985 |

OTHER PUBLICATIONS

Finch, C.A., Polyvinyl Alcohol Developments, "Hydrolysis of Polyvinyl Acetate to Polyvinyl Alcohol," Section 3.3.6—Methyl Acetate Recovery and Acetic Acid Production, John Wiley & Sons, p. 71-73 (1992).
Jones, Jane H., The Cativa TM Process for the Manufacture of Acetic Acid, Platinum Metals Rev., 2000, vol. 44, No. 3, 95-105.

*Primary Examiner*—Paul A. Zucker
(74) *Attorney, Agent, or Firm*—M. Susan Spiering

(57) ABSTRACT

The present invention is directed to using methyl acetate from a vinyl acetate-based or a vinyl-or ethylene-alcohol based polymer or copolymer process directly for use in a methanol carbonylation production process to produce acetic acid, acetic anhydride, or a coproduction of each.

Methyl acetate is a by-product of commercial polyvinyl-alcohol or alkene vinyl alcohol copolymer-based processes. Generally, this material is processed to recover methanol and acetic acid. Discussed herein is a cost-saving scheme to by-pass the methyl acetate processing at production or plant facilities and utilize the methyl acetate in an integrated methanol carbonylation unit. The scheme discussed eliminates an expensive hydrolysis step often associated with the polymer process.

5 Claims, No Drawings

INTEGRATED PROCESS FOR PRODUCING CARBONYLATION ACETIC ACID, ACETIC ANHYDRIDE, OR COPRODUCTION OF EACH FROM A METHYL ACETATE BY-PRODUCT STREAM

RELATED APPLICATIONS

This application claims the benefit of U.S. Provisional Apllication No. 60/347,352, filed Jan. 11, 2002, the entire disclosure of which is hereby incorporated by reference.

BACKGROUND OF THE INVENTION

In the production of vinyl alcohol, or vinyl acetate based polymers or ethylene vinyl alcohol/acetate copolymers, methyl acetate is a byproduct formed. It is desirable to recover the methyl acetate for reuse. The methyl acetate typically produced is impure having a mixture of methyl acetate, methanol, acetic acid, water, solids, and other light impurities. Disclosed is a process wherein prior to use, the methyl acetate is purified.

Methyl acetate can be used for a variety of applications, among them, the production of acetic acid, acetic anhydride or a coproduction of each. The following references provide background regarding production of these materials.

PRIOR ART

U.S. Pat. No. 4,234,718—a cyclic integrated process for production of cellulose acetate from methanol, cellulose, and carbon monoxide is disclosed.

U.S. Pat. No. 4,234,719—a cyclic integrated process for production of cellulose acetate from methanol, cellulose, and carbon monoxide is disclosed.

U.S. Pat. No. 4,352,940—hydrolysis of methyl acetate to acetic acid.

U.S. Pat. No. 4,544,511—process for producing acetic anhydride.

U.S. Pat. No. 5,144,068—Rh catalyzed methanol carbonylation process.

U.S. Pat. No. 5,001,259—Rh catalyzed methanol carbonylation process.

U.S. Pat. No. 5,206,434—purification process for methyl acetate.

U.S. Pat. No. 5,770,770—reactive distillation process and equipment for the production of acetic acid and methanol from methyl acetate hydrolysis.

U.S. Pat. No. 5,831,120—Production of Rh or Ir catalyzed methanol carbonylation acetic acid and replacing at least a portion of the methanol feed with a component selected from the group consisting of methyl acetate, dimethyl ether, acetic anhydride and mixtures thereof. The recovered effluent from this and other processes may be purified of carboxylic acid by reactive distillation with at least one C1 to C3 alcohol.

EP 108437—use of methyl acetate and/or dimethyl ether with carbon monoxide or a mixture of carbon monoxide and hydrogen to form ethylidene diacetate and/or acetic acid anhydride.

EP 087 870—process for the production of acetic anhydride with or without the net coproduction of acetic acid, in a series of esterification, carbonylation, and separation steps.

EP 1061063—(process application); method of producing carboxylic acid and alcohol by obtaining a reaction product liquid by hydrolysis of a carboxylic acid ester in the presence of an acid catalyst and separating said product liquid. Carboxylic acid ester is methyl acetate.

Jp 60-60107—discloses manufacture of poly vinyl alcohol including the saponification of byproduct methyl acetate with carbon monoxide for form acetic anhydride. (English abstract only).

GB 2013184—preparation of vinyl acetate wherein methanol, acetaldehyde and carbon monoxide are reacted in a cyclic integrated process wherein methyl acetate is carbonylated in the first step of the process.

Finch, C A, *Polyvinyl Alcohol Developments*, "Hydrolysis of Polyvinyl Acetate to Polyvinyl Alcohol," Section 3.3.6—Methyl Acetate Recovery and Acetic Acid Production. John Wiley & Sons, p 71–73, (1992).

Jones, Jane H., The Cativa™ Process for the Manufacture of Acetic Acid, Platinum Metals Review, V 44, July 2000, No. 3, 95–105.

DETAILED DESCRIPTION OF THE INVENTION

Polyvinyl alcohol is commercially produced by the reaction of vinyl acetate with a radical initiator and methanol to produce polyvinyl acetate. The poly vinyl acetate is then reacted with methanol in the presence of a base to produce poly vinyl alcohol and methyl acetate. The byproduct of the reaction is methyl acetate. The methyl acetate produced is typically co-mingled in a stream containing methyl acetate, methanol (excess reactant in the above mentioned reaction), light organic impurities, and potentially polymer solids and water.

The methyl acetate is typically converted to acetic acid by hydrolysis. The acetic acid is then sold or can be recycled into vinyl acetate production.

The process to hydrolyze methyl acetate contained in a stream as described above is costly due to capital equipment and energy (operating costs) requirements because of the multiple distillation/separation steps required and expensive materials of construction required by the corrosive environment.

A process in which the methyl acetate stream could be sent directly to a carbonylation process to produce acetic acid (or acetic anhydride or co-production of the acetic acid and acetic anhydride) would eliminate the need for the equipment and energy requirement for hydrolysis. However, the methyl acetate stream is not suitable to be directly fed to the carbonylation process. The art generally does not address the issue of impure methyl acetate and the need to purify prior to recycle in a cyclic integrated process. The methyl acetate itself is unsuitable as feed to a carbonylation unit without removal or treatment of impurities. If not removed, the methyl acetate impurities lead to problems in downstream use. The polymer solids must be removed, as the solids would foul the carbonylation process. The water content must be adjusted to be appropriate for the product being produced. For example, if acetic acid is being produced by carbonylation, then no more than one molecular unit of water may enter the reactor per unit of methyl acetate. Otherwise, dry acetic acid is not produced.

The present invention relates to integrating the processes of vinyl alcohol or ethylene vinyl alcohol based—or vinyl acetate based-polymer or copolymers, e.g., polyvinyl alcohol production with a carbonylation process so that methyl acetate produced in the first process, for example the poly vinyl alcohol production, is converted to a saleable product at a significant reduction in energy cost, or alternatively can be fed into the reaction system for use in the production of acetic acid, acetic anhydride, or coproduction of each.

Alternatively, the present invention is directed to use of methyl acetate produced as a byproduct in the polyvinyl alcohol process in the reaction to produce acetic acid, anhydride, or coproduction of each. An exemplified integrated process would involve production of acetic acid, which would be used to produce vinyl acetate. The vinyl acetate produced would be used in the reaction to produce polyvinyl alcohol. The methyl acetate byproduct would be purified and fed directly to the production of acetic acid, anhydride, or coproduction thereof. Hence the process is integrated from acetic acid production through polyvinyl alcohol production, including use of byproducts formed in intermittent reactions.

To effect the process integration, a suitable purification step is required for the methyl acetate. A process has been demonstrated wherein streams from the polyvinyl alcohol polymer process were recovered and refined for feed to a methanol carbonylation acetic acid process. For example, the stream containing methyl acetate, methanol, water, light impurities, and polymer solids was purified by separation/distillation. Excess water and polymer solids were removed while organic losses in the aqueous stream kept to a low level. Other aqueous/organic streams which contain a subset of the above listed components could also be purified/processed. The product of the purification step is a stream generally containing methanol, methyl acetate, acceptable level of impurities, essentially no polymer solids, and sufficiently low amounts of water. The impurities or amounts thereof, as well as the water concentration can vary based on the desired application and the equipment in use. Typically, for methyl acetate to be used in a methanol carbonylation unit for production of acetic acid, it is recommended that no more than about one molecular unit of water per molecular unit of methyl acetate be present in the stream.

The invention will be described with more particularity in relation to the production of acetic acid from polyvinyl alcohol but it is recognized by those of skill in the art that production of acetic anhydride or coproduction of acetic acid and acetic anhydride can also be produced from the methyl acetate formed. Acetic acid, anhydride, or coproduction of each may be produced by a variety of methods well known in the art. The present invention is not directed with the manner of making the acid or coproduction of acid and anhydride, but with the integrated process allowing use of a purified or treated methyl acetate.

When acid, anhydride or coproduction of each is produced by the method of methanol carbonylation, either employing rhodium or iridium as a catalyst, water and impurity levels in the methyl acetate are a concern. This is because the rate of generation of water by methanation of the methanol and/or reactive derivative in the carbonylation reactor is relatively high and can be greater than the rate of consumption of water by the water gas shift reaction in the carbonylation reactor. The methanolysis can be shown as:

$$CH_3OH+H_2 \rightarrow CH_4+H_2O$$

The water gas shift reaction can be shown as:

$$CO+H_2O \rightarrow CO_2+H_2$$

Water may accumulate in the continuous production of acetic acid or acetic anhydride or coproduction thereof, by direct or indirect ingress into the reactor system. The removal of excess water or control of the water balance in carbonylation processes is the subject of numerous references. However, a problem with water removal is the simultaneous removal of components such as methyl iodide. The methyl iodide can be recycled into the reaction, or disposed. If disposed, it must be disposed of properly due to environmental concerns. It is desirable that the methyl acetate employed in the present process has minimal amounts of water. It is critical in making acetic acid in a carbonylation unit that the water be present in less than stoichometric proportion relative to the methyl acetate content. If making acetic anhydride, it is desired that no water, or methanol, be present. With respect to methanol during the production of acetic acid, methanol concentration is not as large a concern as water concentration.

An additional concern with the use of methyl acetate from a vinyl- or ethylene-alcohol or vinyl acetate-based process is the carbonyl content in the stream. Carbonyl impurities include acetaldehyde, acetone, methyl ethyl ketone, butyraldehyde, crotonaldehyde, 2-ethyl crotonaldehyde, and 2-ethyl butyraldehyde and the like, as well as unsaturated aldehydes. Additional impurities to be considered in the methyl acetate stream can include toluene, benzene, acetone, dimethyl acetal, 3-methyl-2-pentanone, propionic acid, ethyl acetate and ethanol.

An embodiment of the present invention involves a process for using a methyl acetate stream in a methanol carbonylation process comprising:
a) producing a vinyl acetate based polymer or copolymer which is hydrolyzed; or
b) alternatively producing a polymer or copolymer of vinyl alcohol which undergoes a subsequent methanolysis;
c) forming a methyl acetate byproduct;
d) directing the methyl acetate to a purification process;
e) directing the purified methyl acetate to a methanol carbonylation process.

The above embodiment may also be performed utilizing an alkene, or more particularly ethylene as a comonomer.

The methyl acetate by product formed may be a mixture of methanol, acetic acid, water, light organic impurities, and some polymer solids. Methods to purify the methyl acetate include, but are not limited to, separation of the water, impurities and solids via distillation, extraction, filtration or crystallization.

An alternate embodiment of the invention involves a process for using methyl acetate comprising
a) producing acetic acid;
b) contacting the acetic acid with reactants under conditions sufficient to form vinyl acetate;
c) contacting the vinyl acetate under conditions sufficient to form poly vinyl acetate;
d) contacting the poly vinyl acetate with a base and methanol under conditions sufficient to form poly vinyl alcohol and methyl acetate as a byproduct;
e) treating the methyl acetate sufficient to remove at least some of the impurities therewith;
f) directing the methyl acetate to an acetic acid production process.

Yet another embodiment of the invention involves a process for using methyl acetate comprising
a) producing acetic anhydride;
b) contacting the acetic anhydride with reactants under conditions sufficient to form vinyl acetate;
c) contacting the vinyl acetate in under conditions sufficient to form poly vinyl acetate;
d) contacting the poly vinyl acetate with a base and methanol under conditions sufficient to form poly vinyl alcohol and methyl acetate as a byproduct;

e) treating the methyl acetate sufficient to remove at least some of the impurities therewith;

f) directing the methyl acetate to an acetic anhydride production process.

Yet another embodiment of the invention involves a process for using methyl acetate comprising a) coproducing acetic acid and acetic anhydride;

b) contacting the acetic acid and acetic anhydride with reactants under conditions sufficient to form vinyl acetate;

c) contacting the vinyl acetate in under conditions sufficient to form poly vinyl acetate;

d) contacting the poly vinyl acetate with a base and methanol under conditions sufficient to form poly vinyl alcohol and methyl acetate as a byproduct;

e) treating the methyl acetate sufficient to remove at least some of the impurities therewith;

f) directing the methyl acetate to a coproduction process for production of acetic acid and acetic anhydride.

In the production of poly vinyl alcohol (PVOH), the resultant methyl acetate formed is considered a mother liquor to be ultimately purified and fed to a methanol carbonylation reactor for the production of acetic acid. The crude methyl acetate mixture is directed to a mother liquor column for purification to remove impurities such as light organic components, polymeric solids and water. The column is operated at elevated pressure, and heated, to remove essentially all of the methyl acetate in an overhead stream in purified form, and over 95% of the methanol from the impure methyl acetate crude mixture. The reflux of the column is adjusted to maintain about one mole of water for every mole of methyl acetate in the column overhead. The polymeric solids typically consist of poly vinyl acetate, poly vinyl alcohol, and sodium acetate and exit from the bottom of the mother liquor column as a residue.

By operating the Mother Liquor Column at an elevated pressure, the overhead components or overheads can be used as a heat source for other recovery columns in the polyvinyl alcohol plant. Operating at about 55 psig allows for over 50% of the energy used in this tower to be recovered. Other streams may additionally be sent to the mother liquor column for separation. For example, a stream containing water and methanol from the extractive distillation of vinyl acetate and methanol, which is often used in the PVOH process can also be sent to the mother liquor column for separation.

When the proposed mother liquor column is used, a column to separate methanol and water could be retained in the PVOH process. The stream from the extractive distillation could be forwarded to the methanol water column, or a mother liquor column. The mother liquor column, or an extractive distillation, could then be operated in a mode where a portion or all of the methanol in the feed was allowed to exit the column bottom with the water and solids. The column bottoms, or residue could be forwarded to the methanol water column. This mode of operation may find use in the overall plant cost optimization if the cost of transporting the mother liquor column overhead stream was large.

EXAMPLES

Example 1

A distillation was conducted using streams from a PVOH process. In the laboratory, a 40 tray Oldershaw column was employed at elevated pressure and temperature. A mother liquor stream containing 0.24 wt % solids was fed about midway on the column, while an aqueous methanol stream containing 0.13 wt % solids was fed to the column about one third from the base. In the atmospheric distillation the overhead and the base temperatures were 68 C and 100 C, respectively. The mother liquor feed rate was 13.7 g/min and the aqueous methanol feed rate was 11.5 g/min. The reflux ratio was maintained at about 0.23. No foaming or major fouling problems in the reboiler were observed during the distillation. Dark brown/black staining or fouling was observed from around tray 15 to the base. However, this minor fouling did not plug the small tray holes or downcomers of the Oldershaw column. The trays above the mother liquor feed were clean.

The analysis of the feed, overhead methanol/methyl acetate product, and the wastewater residue is given in Table 1 below.

Purified methyl acetate was employed in the production of methanol carbonylation acetic acid Acetic acid was produced having no atypical impurities or impurity profile.

TABLE 1

Analysis of laboratory experiment on distillation of feed methanol/methyl acetate mixture.

| Component | Mother Liquor Feed | Aqueous Methanol Feed | Product | Residue |
|---|---|---|---|---|
| Water (wt %) | 21.4 | 82.5 | 5.3 | 100 |
| Methanol (wt %) | 55.3 | 17.5 | 66.8 | 0.0656 |
| Methyl Acetate (wt %) | 27.1 | Nd | 27.9 | nd |
| Ethanol (ppm) | 1476 | 75 | 1704 | nd |
| Acetone (ppm) | nd | Nd | Nd | 16 |
| Dimethyl Acetal (ppm) | 17 | Nd | 22 | nd |
| Ethyl Acetate (ppm) | 315 | Nd | 366 | nd |
| Acetaldehyde (ppm) | 248 | Nd | 313 | nd |
| Toluene (ppm) | nd | Nd | 74 | nd |
| Acetic Acid (ppm) | 45 | Nd | Nd | 87 |
| Alkanes (ppm) | <100 | 781 | 3 | 932 |

Nd = non-detected; values are not normalized.
Product = Methyl Acetate, Methanol Product of Invention The example illustrates that a methanol/methyl acetate stream could be purified at a low reflux ratio with less than 1000 ppm methanol and less than 2600 ppm alkanes in the waste water.

Example 2

The methanol/methyl acetate product of example 1 was fed to an experimental carbonylation unit in the following manner: Prior to feeding the material from example 1 to the methanol carbonylation experimental unit, the experimental unit was brought to steady state using pure methanol feed at 195° C., 1100 ppm Rh, 2.2 wt % MeOAc, 2.2 wt % $H_2O$, 6.5 wt % MeI. The resulting space time yield was 20 mols/L/hr. Reaction conditions were held constant and the distillate from example 1 replaced MeOH as feed to the experimental unit. Water was added to the experimental unit such that total water in the feed was equimolar to the total methyl acetate in the feed. These conditions were maintained for three days. The reaction rate remained unchanged at 20 mols/L/hr. The composition of the acetic acid product from the experimental unit is listed in the table below. The concentration of propionic acid (HOPr) in the product increased after feeding material from example 1.

TABLE 2

| Product From Example 2 | |
| --- | --- |
| methanol | 189 ppm |
| methyl acetate | 53 ppm |
| crotonaldehyde | 1.4 ppm |
| butyraldehyde | 6 ppm |
| 2-ethylcrotonaldehyde | 5.2 ppm |
| propionic acid | 1601 ppm |
| Acetic Acid | Balance |

The invention claimed is:

1. A process for using a methyl acetate stream in a methanol carbonylation process comprising:
   a) producing a vinyl acetate based polymer or copolymer;
   b) contacting the vinyl acetate based polymer or copolymer with a base and methanol under conditions sufficient to form a polymer or copolymer of vinyl alcohol and a methyl acetate byproduct stream;
   c) directing the methyl acetate byproduct stream to a purification process comprising extractive distillation to form a purified methyl acetate stream; and,
   d) directing the purified methyl acetate stream to a methanol carbonylation process.

2. The process of claim 1 wherein the methyl acetate byproduct stream comprises methyl acetate, methanol, light organics, polymer solids and water.

3. The process of claim 1 wherein the purified methyl acetate stream comprises methyl acetate, methanol and water.

4. The process of claim 1 wherein the purified methyl acetate stream comprises methyl acetate and water, with the concentration of water in the purified methyl acetate stream being limited to no more than an equimolar ratio with methyl acetate.

5. The process of claim 1 wherein the extractive distillation is operated so as to maintain about one mole of water for every mole of methyl acetate in the purified methyl acetate stream.

* * * * *